(12) United States Patent
Brown

(10) Patent No.: US 6,518,566 B1
(45) Date of Patent: Feb. 11, 2003

(54) HIGH-VOLUME SPECIMEN BLOCK STORAGE SYSTEM AND MODULAR STORAGE RECEPTACLE

(76) Inventor: Stanley Brown, 4601 Henry Hudson Pkwy. - Apt. B11, Riverdale, NY (US) 10471

( * ) Notice: Subject to any disclaimer, the term of this patent is extended or adjusted under 35 U.S.C. 154(b) by 43 days.

(21) Appl. No.: 09/715,607

(22) Filed: Nov. 20, 2000

(51) Int. Cl.[7] .................................................. H01J 5/02
(52) U.S. Cl. ...................................... 250/239; 356/244
(58) Field of Search ......................... 250/239; 356/244, 356/245, 246

(56) References Cited

U.S. PATENT DOCUMENTS 3,768,914 A * 10/1973 Kinney et al. .............. 356/244
5,048,957 A * 9/1991 Berthold et al. ............ 356/246

* cited by examiner

Primary Examiner—Hung Xuan Dang
(74) Attorney, Agent, or Firm—Scully, Scott, Murphy & Presser

(57) ABSTRACT

A specimen block storage module containing a plurality of shaped cavities into which each of a plurality of specimen blocks "snap", i.e., are mechanically held in place by structural projections or detents formed on the cavity walls, thus eliminating the possibility of inadvertent dislodgement. Each cavity is indexed, e.g., by letter and number, providing for the rapid, accurate identification of every individual block. Each of the modules has on its undersurface a pressure sensitive adhesive which permits the module to be attached to any appropriate surface; e.g., the inside bottom of a fitted box, or in any combination desired onto a specially-designed, suitably-sized and preferably covered panel that fits into a protective binder (e.g., a standard three-ring binder) for holding a plurality of the panels in the desired order. Many such panels can be stored in a single binder, separated by indexed dividers on which data can be recorded, and, as a consequence of the "snap-in" feature, the binders can be stored in an upright position without the blocks becoming dislodged.

24 Claims, 7 Drawing Sheets

US 6,518,566 B1

HIGH-VOLUME SPECIMEN BLOCK STORAGE SYSTEM AND MODULAR STORAGE RECEPTACLE

BACKGROUND OF THE INVENTION

In the field of electron microscopy, biological material in the form of very small pieces of tissue approximately 1 millimeter square (specimens) are embedded in polymeric substances such as epoxy or methacrylate resins. These resins are then hardened into rod-like shapes by exposure to heat or ultraviolet radiation, while in polyethylene molds such as the well known BEEM® capsule. When the capsule is removed, these hardened rods present the specimen at the apex of a pyramid, the face of which is approximately 1 millimeter square. The rods are called specimen blocks or simply blocks by electron microscopists. The blocks are placed in an ultramicrotome, where thin sections approximately 66–90 millimicrons thick are cut from the pyramidal face and mounted on ⅛" diameter copper grids for viewing in the electron microscope. While much attention has been paid to devices for the safe storage of the grids (see U.S. Pat. No. 3,353,656 and U.S. Pat. No. 3,768,914), little has been done to provide the same protection, identification and organization for the blocks. The specimen-bearing tips of these blocks are vulnerable to damage prior to sectioning, and even more vulnerable after sectioning when the tissue inside has been exposed.

At present, no commercially available block storage system exists other than the BEEM® modular specimen storage receptacle (U.S. Pat. No. 3,353,656) that allows for the safe storage and identification of these blocks. This early BEEM® modular storage receptacle, while effective, has two drawbacks:

(1) it is a low volume device, providing space for only two blocks while there are usually many blocks associated with a given experiment.

(2) the two blocks merely 'rest' in their cavities and can be inadvertently dislodged whenever the module is open.

BRIEF SUMMARY OF THE INVENTION

The present invention serves to overcome the above shortcomings, and is embodied in and carried out by a block storage module containing a plurality of shaped cavities into which the blocks "snap", i.e., are mechanically held in place by structural projections or detents formed on the cavity walls at or near the open end of the cavity, thus eliminating the possibility of inadvertent dislodgement. Each cavity is indexed by letter and number providing for the rapid, accurate identification of every individual block. Each of the modules has on its undersurface a pressure sensitive adhesive which permits the module to be attached to any appropriate surface; i.e., the inside bottom of a fitted box, or in any combination desired onto a specially-designed and suitably-sized (e.g., 8"×11") panel that fits into a protective binder (e.g., a standard three-ring binder) for holding a plurality of the panels in any desired order. Many such panels can be stored in a single binder, separated by indexed dividers on which any relevant data can be recorded, and, as a consequence of the "snap-in" feature, the binders can be stored in an upright position without fear of the blocks becoming dislodged. The panels are each preferably covered with an overlying cover that is secured both to the binder and to the associated panel. Each cover is preferably clear to enable the user to read the indicia on the underlying modules. This arrangement provides a safe, compact, and infinitely expandable high-volume specimen storage system.

BRIEF DESCRIPTION OF THE DRAWINGS

The present invention will be better understood when the written description thereof is read with reference to the accompanying drawings, of which.

DETAILED DESCRIPTION OF THE INVENTION

Figure 1:
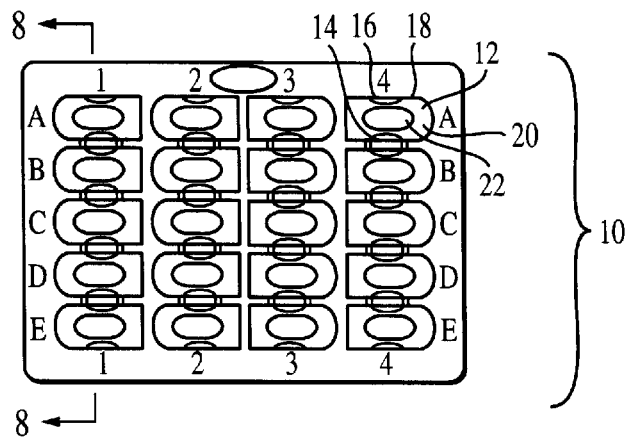
FIG. 1 shows a plan view of a specimen block storage module for holding a number of rectangular specimen blocks in two groups of tip-to-end-oriented blocks.
Figure 8:
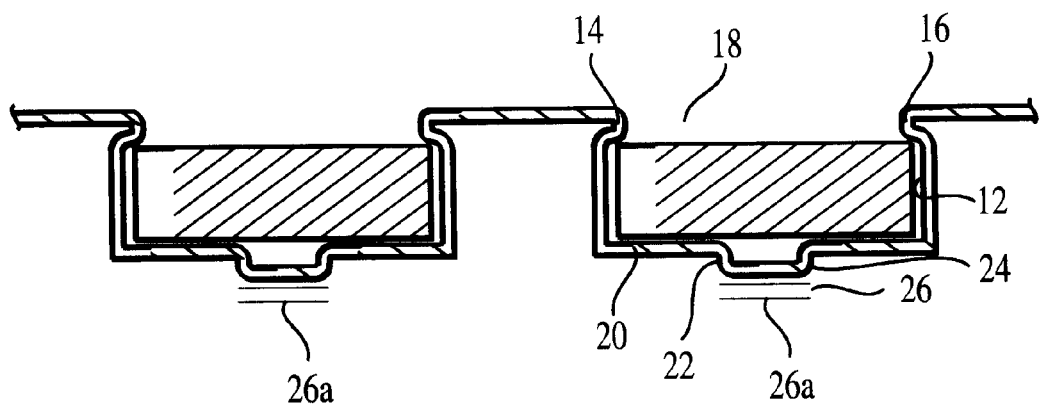
FIG. 8 shows a cross-sectional view of the specimen block storage module of FIG. 1 along lines 8—8 of FIG. 1.

In FIGS. 1 and 8, there is shown a specimen block storage module 10 capable of holding a number of rectangular specimen blocks in two groups of tip-to-end-oriented block. Each specimen block is secured in a shaped cavity 12 by a pair of opposed protrusions 14, 16 positioned at the open end 18 of cavity 12. At the closed end 20 of each cavity 12 is an extension 22 with a flat surface 24, each one of said flat surfaces 24 being coplanar with each other of said flat surfaces 24. Alternatively, since the closed end 20 of each shaped cavity 12 is flat and coplanar with each other closed ends 20, this embodiment could be formed without the extensions 22. Each of the shaped cavities 12 has associated locating indicia. In this embodiment, the columns are designated by numbers at the top and bottom of each column, and the rows are designated by letters. As shown in FIG. 8, a double-sided-adhesive overlay 26 is affixed to each one of said flat surfaces 24 to enable the specimen block storage module 10 to be mounted on a panel. Each overlay 26 includes a protective peel-away sheet 26a on its outer (lower) surface for removal just prior to mounting on a panel by pressing the exposed adhesive surfaces against the receiving surface of the panel. The protective peel-away sheets 26a are preferably interconnected for quick and easy simultaneous removal.

Figure 2:
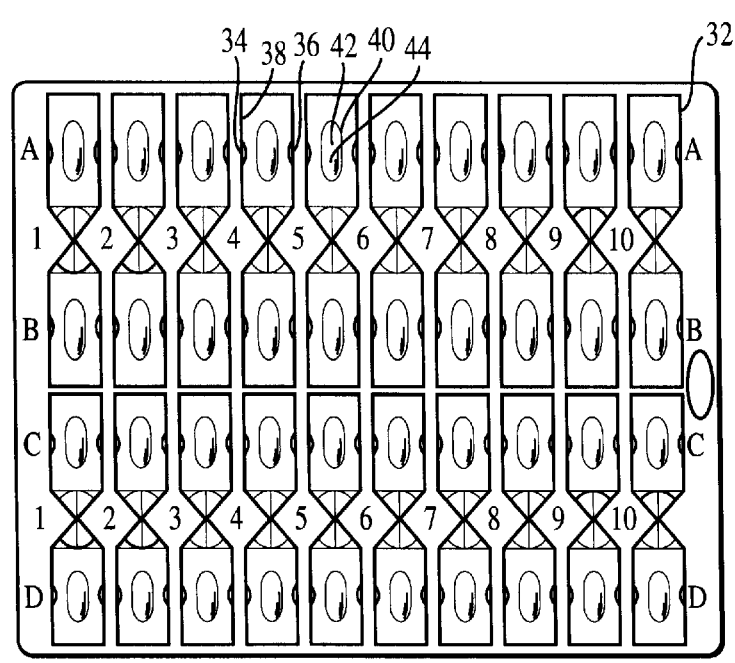
FIG. 2 shows a plan view of a specimen block storage module for holding a number of specimen blocks in two groups of tip-to-tip-oriented blocks.

In FIG. 2, there is shown a specimen block storage module 30 capable of holding a number of generally-cylindrical specimen blocks, with either conical or pyramidal tips, in groups of tip-to-tip-oriented blocks. Each specimen block is secured in a shaped cavity 32 by a pair of opposed protrusions 34, 36 positioned at the open end 38 of cavity 32. Each of the shaped cavities 32 has associated locating indicia. In this embodiment, the columns are designated by numbers positioned adjacent the tips of the specimen block, and the rows are designated by letters. At the closed end 40 of each cavity 32 is an extension 42 with a flat surface 44, each one of said flat surfaces 44 being coplanar with each other of said flat surfaces 44. The means of attachment to a mounting panel may be in the form shown in either FIG. 5 or FIG. 7.

Figure 3:
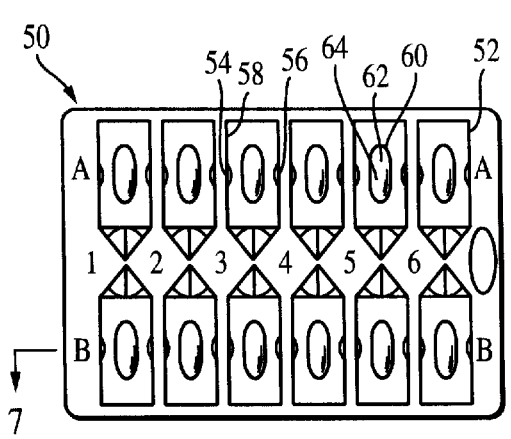
FIG. 3 shows a plan view of a specimen block storage module for holding a smaller number of specimen blocks in two groups of tip-to-tip-oriented blocks.
Figure 7:
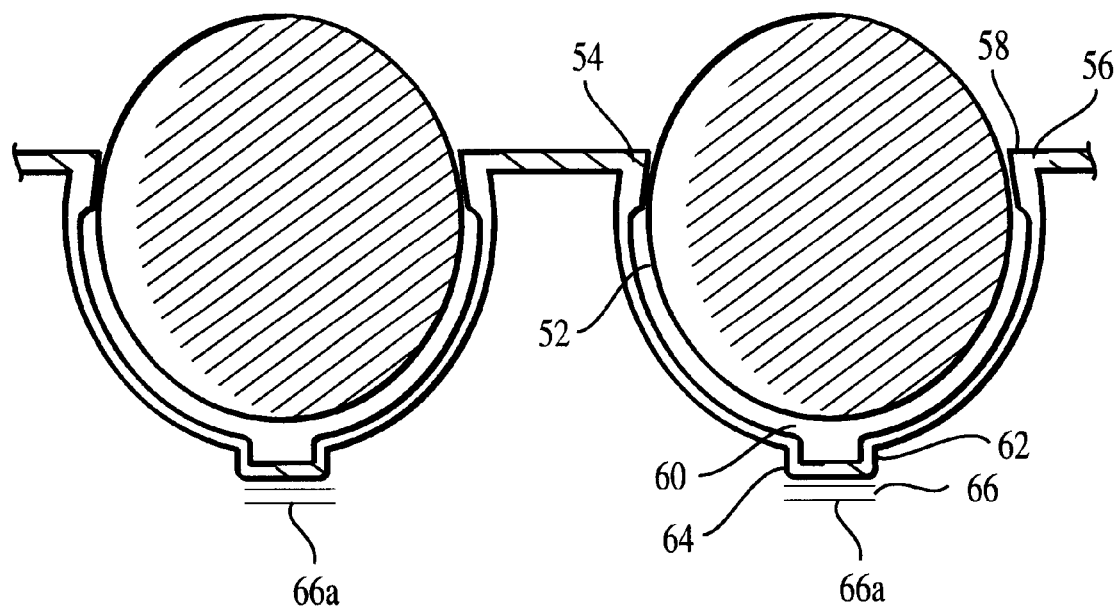
FIG. 7 shows a cross-sectional view of the specimen block storage module of FIG. 3 along lines 7—7 of FIG. 3.

In FIGS. 3 and 7, there is shown a specimen block storage module 50 capable of holding a number of generally-cylindrical specimen blocks, with either conical or pyramidal tips, in groups of tip-to-tip-oriented blocks. Each specimen block is secured in a shaped cavity 52 by a pair of opposed protrusions 54, 56 positioned at the open end 58 of cavity 52. At the closed end 60 of each cavity 52 is an extension 62 with a flat surface 64, each one of said flat surfaces 64 being coplanar with each other of said flat surfaces 64. As shown in FIG. 7, a double-sided-adhesive overlay 66 is affixed to each one of said flat surfaces 64 to enable the specimen block storage module 50 to be mounted on a panel. Each double-sided-adhesive overlay 66 includes a protective peel-away sheet 66a on its outer (lower) surface for removal just prior to mounting on a panel by pressing the exposed adhesive surfaces against the receiving surface of the panel. The protective peel-away sheets 66a are preferably interconnected for quick and easy simultaneous removal.

Figure 4:
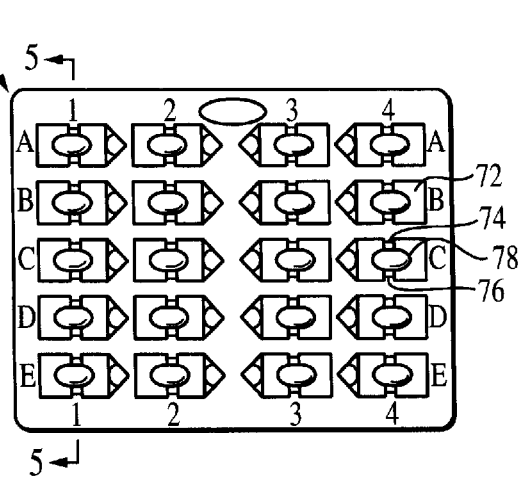
FIG. 4 shows a plan view of a specimen block storage module for holding a number of specimen blocks in two groups of tip-to-end-oriented blocks.
Figure 5:
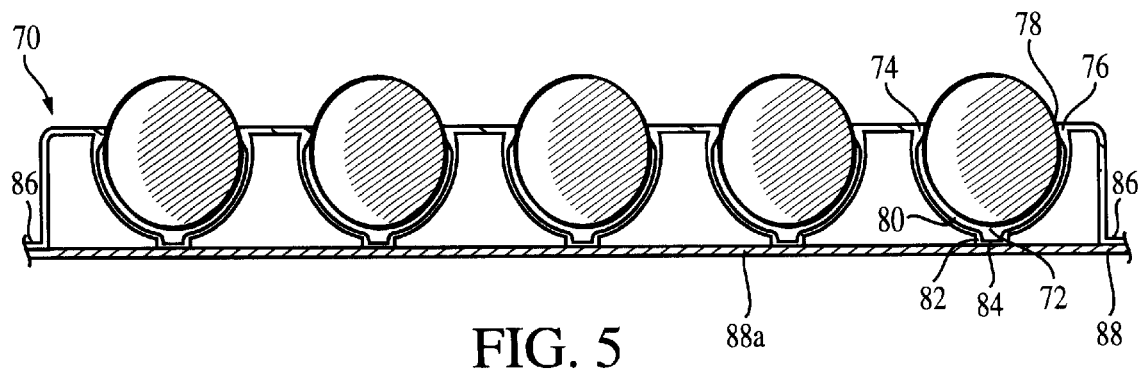
FIG. 5 shows a cross-sectional view of the specimen block storage module along lines 5—5 of FIG. 4.

In FIGS. 4 and 5, there is shown a specimen block storage module 70 capable of holding a number of generally-cylindrical specimen blocks, with either conical or pyramidal tips, in two groups of tip-to-end-oriented blocks. Each specimen block is secured in a shaped cavity 72 by a pair of opposed protrusions 74, 76 positioned at the open end 78 of cavity 72. At the closed end 80 of each cavity 72 is an extension 82 with a flat surface 84, each one of said flat surfaces 84 being coplanar with each other of said flat surfaces 84. A rim 86 extends laterally, its bottom surface being coplanar with the flat surfaces 84 of extensions 82. An double-sided-adhesive sheet 88 is affixed to each one of said flat surfaces 84 and the coplanar bottom surface of rim 86 to enable the specimen block storage module 70 to be mounted on a panel by pressing the exposed adhesive surface against the receiving surface of the panel. The double-sided-adhesive sheet 88 includes a protective peel-away sheet 88a on its outer (lower) surface for removal just prior to mounting on a panel.

Figure 6:
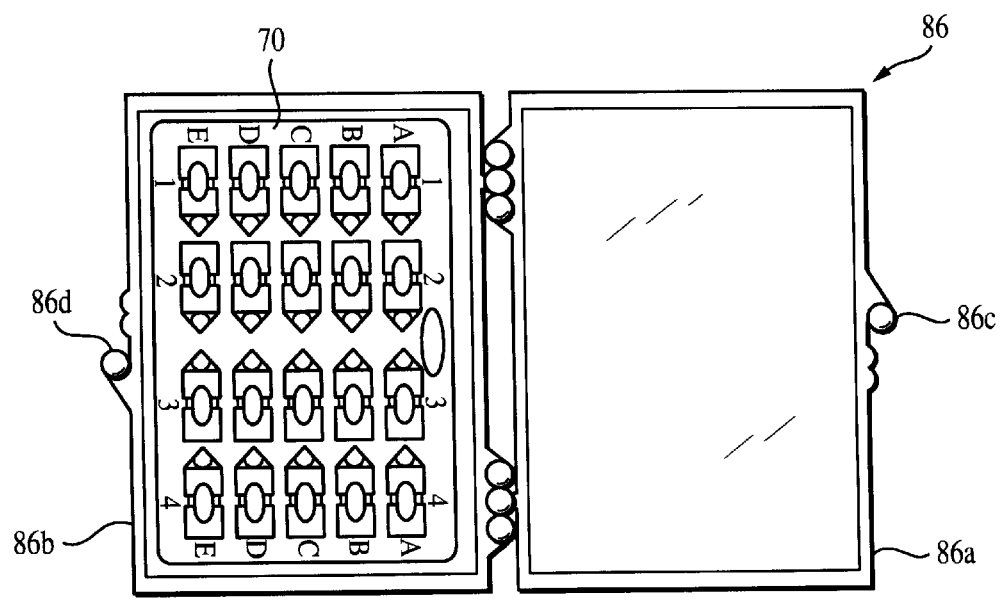
FIG. 6 shows a plan view of the specimen block storage module of FIGS. 4 and 5 in a storage box with a hinged cover.

In FIG. 6, the specimen block storage module 70 of FIGS. 4 and 5 is shown in a storage box 86 having a hinged cover 86a and a bottom panel 86b. The box may be latched closed by interengaging clasp members 86c and 86d on the hinged cover 86a and bottom panel 86b, respectively.

Figure 9:
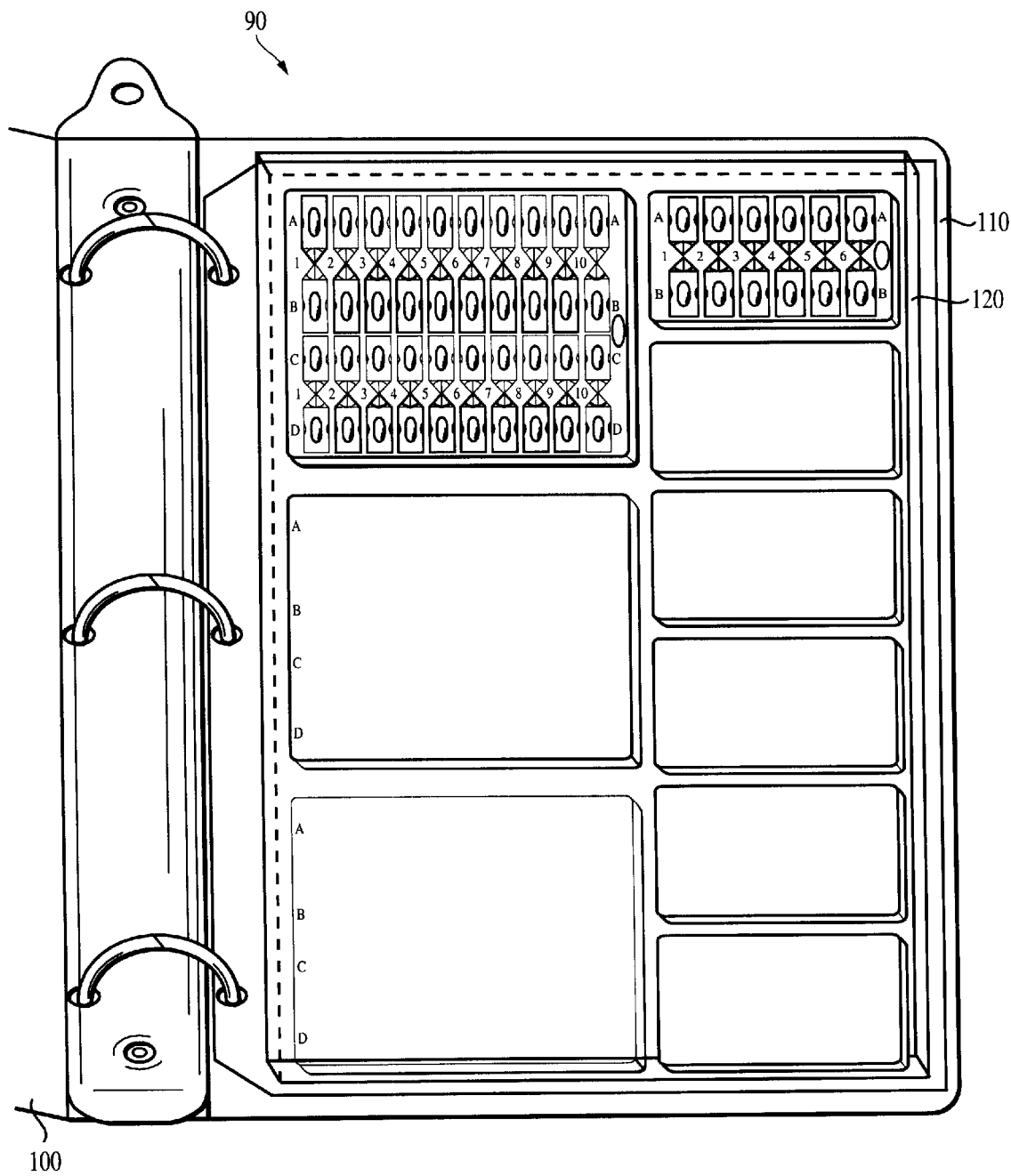
FIG. 9 shows an isometric view of the high-volume specimen block storage system, with specimen block storage modules positioned in covered panels removably affixed to a binder.

In FIG. 9, there is shown a high-volume specimen block storage system 90 comprising a protective binder 100 for holding in the desired order a plurality of the panels 110 enclosing one or more storage modules, each panel 110 with an overlying protective clear cover 120. The panels 110 are removably affixed to binder 100 by any conventional multiple-ring mechanism. Many such panels can be stored in a single binder 100, optionally separated by indexed dividers on which data can be recorded, and, as a consequence of the earlier-mentioned "snap-in" feature of the storage modules, the binders 100 can be stored in an upright position without the blocks becoming dislodged. This arrangement provides a safe, compact, and infinitely expandable high-volume specimen storage system.

Figure 10:
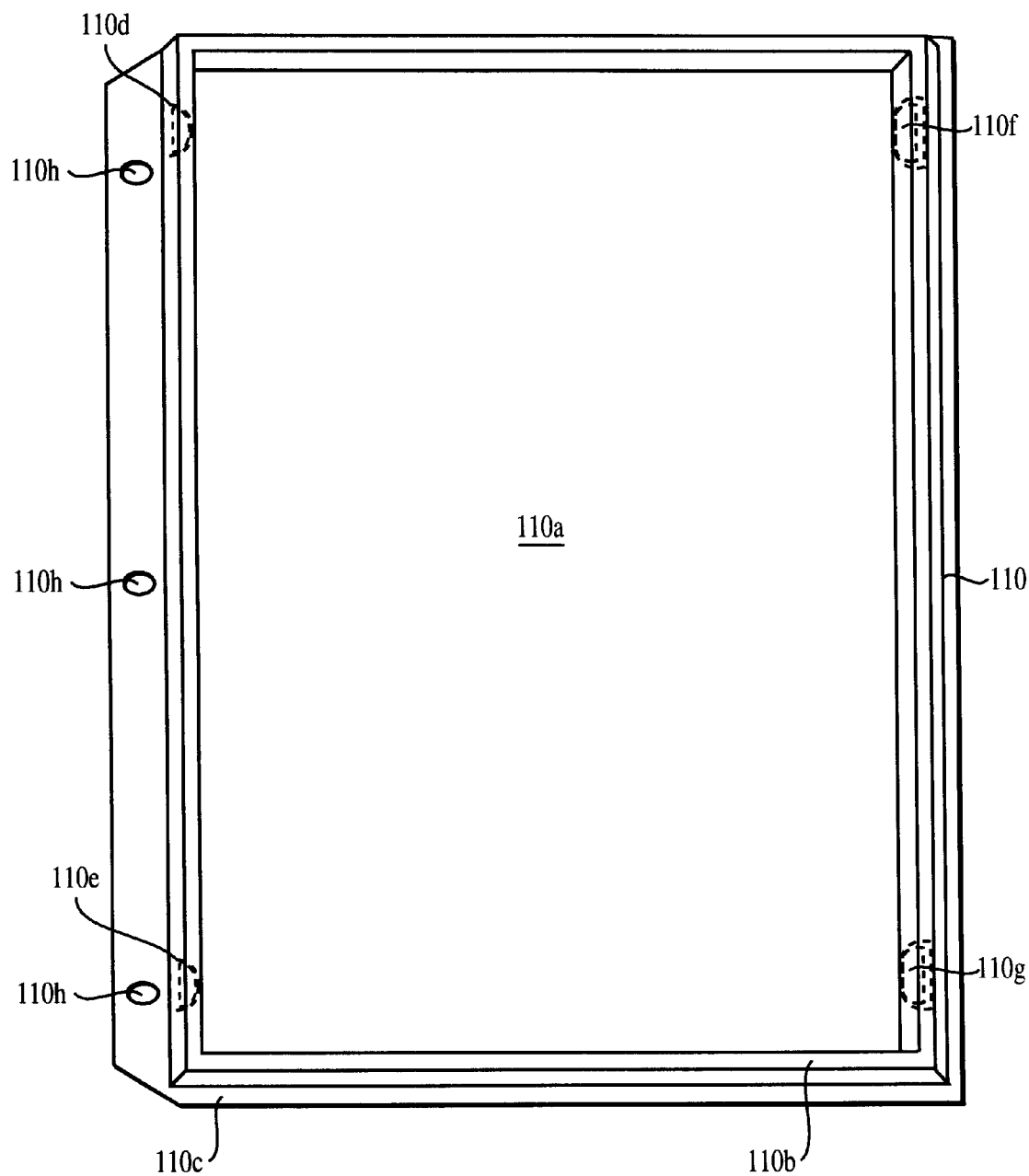
FIG. 10 shows an isometric view of a panel, removed from the associated cover and removed from the binder.

In FIG. 10, there is shown an isometric view of a panel 110, separated from the associated cover 120 and removed from the ring binder 100. The panel 110 is preferably opaque, while the overlying cover 120 is clear to enable reading of the indicia on the storage modules. The panel 110 has a flat portion 110a on which the storage modules are mounted, with a folded ridge 110b and a peripheral rim 110c. Slots 110d, e, f, g are formed in the outer surface of the ridge 110b near its corners, and preferably in opposed pairs 110d, f and 110e, g. The peripheral rim 110c widens at the left to permit the formation of holes 110h to enable mounting in ring binder 100.

Figure 11:
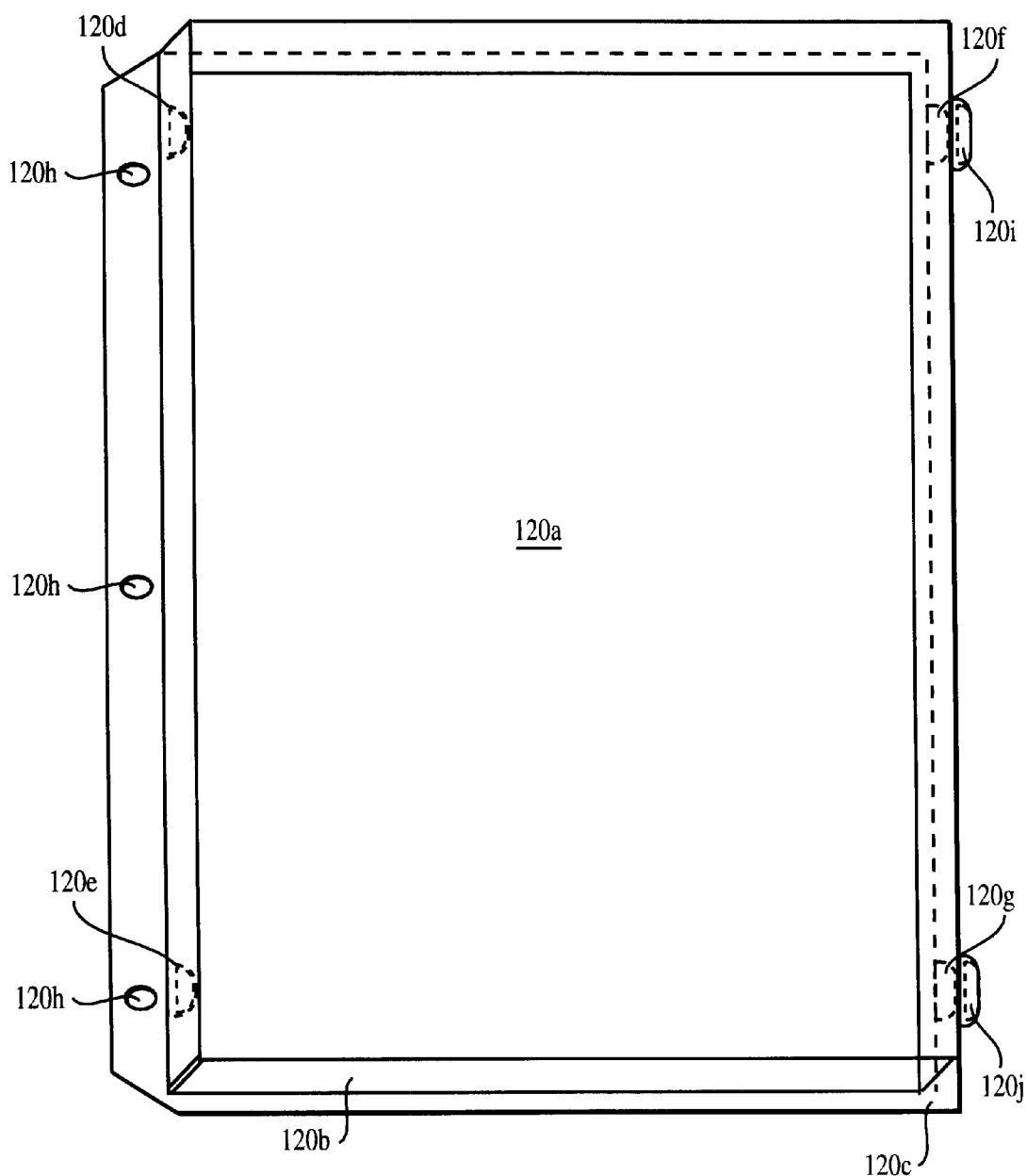
FIG. 11 shows an isometric view of a cover, removed from the associated panel and removed from the binder.

In FIG. 11, there is shown an isometric view of a cover, detached from the associated panel and removed from the ring binder 100. The cover 120 comprises a flat top portion 120a, which is generally parallel to the flat portion 110a of panel 110 when the cover 120 is in place, and further comprises a four-sided peripheral portion 120b with a rim 120c extending laterally from the bottom edge of peripheral portion 120b. The peripheral portion 120b of the cover 120 has indents 120d, e, f, g formed therein to engage with slots 110d, e, f, g in the outer surface of the ridge 110b of panel 110. Thus, a tight seal is formed by engagement of peripheral portion 120b of cover 120 with the outer surface of the ridge 110b of panel 110, and that seal is secured by the engagement of the indents 120d, e, f, g of cover 120 with slots 110d, e, f, g in the outer surface of the ridge 110b of panel 110. The tabs 120i and 120j facilitate removal of the cover 120 from the panel 110. The peripheral rim 120c widens at the left to permit the formation of holes 120h to enable mounting in ring binder 100.

Figure 12:
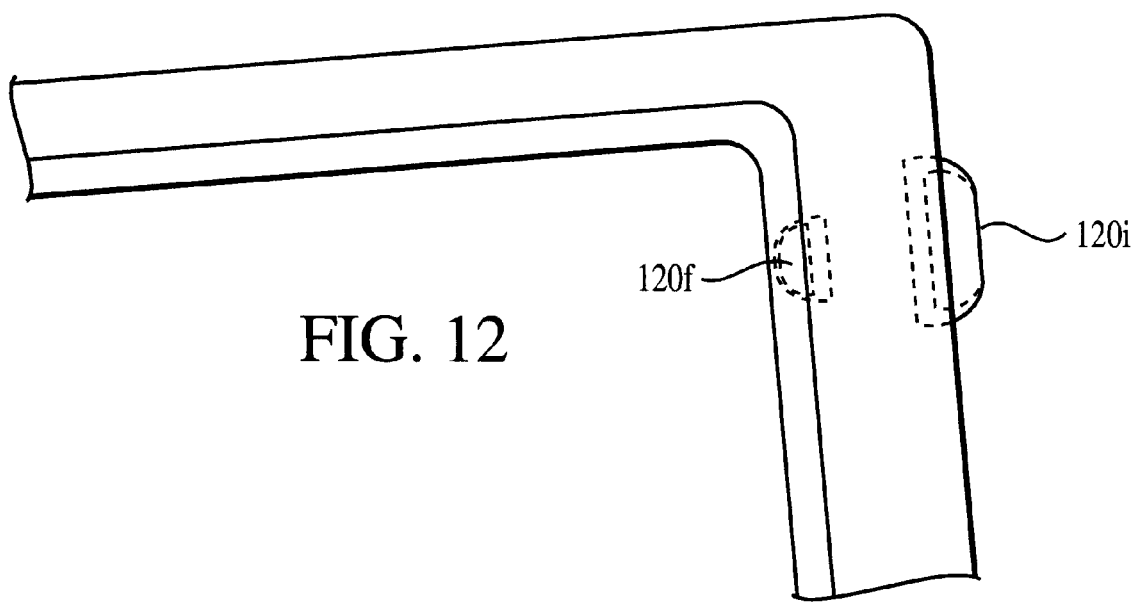
FIG. 12 shows a partial view of the panel combined with its overlying cover.

FIG. 12 is a partial view of the panel 110 combined with its overlying cover 120, showing the fit of indent 120f into slot 110f as they would be seen if viewed from above the combined panel 110 and cover 120.

Figure 13:
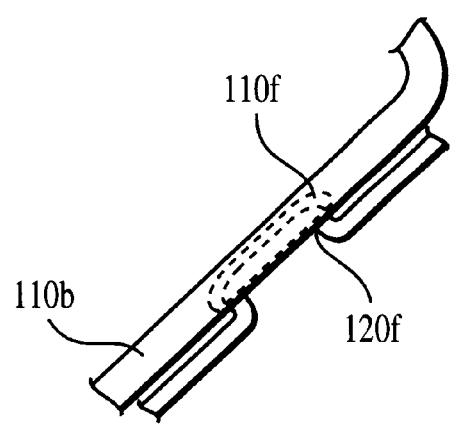
FIG. 13 shows the interlocking detents of the panel and its overlying cover.

FIG. 13 is a partial view of the panel 110 combined with its overlying cover 120, showing in detail the fit of indent 120f into slot 110f and the sealing abutment of ridge 110b and the outer surface of peripheral portion 120b.

Certain modifications and variations of the disclosed embodiments of the present invention will be apparent to those skilled in the art. For example, in the specimen block storage module shown in FIGS. 1 and 8, and in the specimen block storage module shown in FIGS. 2, 3, 4, 5 and 7, the extension at the closed end of each cavity could be eliminated, with an adhesive-coated rim being the sole means of affixing the storage module to a panel. The inverse is also true, i.e., the rim could be eliminated, with adhesive-coated extensions at the closed end of each cavity being the sole means of affixing the storage module to a panel. Also, the relative positions of the indents 120d, e, f, g and the cooperating slots 110d, e, f, g could be reversed, i.e., the indents 120d, e, f, g of cover 120 could be formed as protuberances on the ridge 110b of panel 110, with slots 110d, e, f, g being formed in cover 120. It should be understood that the disclosed embodiments are intended to be illustrative only, and not in any way restrictive of the scope of the invention as defined by the claims set forth hereunder.

I claim:

1. A system for organizing and protecting specimen blocks, comprising:
   (a) at least one specimen block storage module, comprising: a plurality of indentations forming cavities shaped for receiving and retaining a plurality of specimen blocks regardless of the spatial orientation of the specimen block storage module; an underside beneath said plurality of shaped cavities; and means for securing said at least one specimen block storage module to a mounting surface;
   (b) at least one panel comprising a mounting surface on which at least one specimen block storage module is affixed, and means for securing said at least one panel in a binder; and
   (c) a binder for retaining a plurality of said panels in a selected order.

2. The system according to claim 1, wherein each of said shaped cavities of said at least one specimen block storage module comprises an open end and a closed end, and includes opposed structural projections formed at said open end of said cavity.

3. The system according to either claim 1 or 2, wherein each of said shaped cavities of said at least one specimen block storage module is shaped to receive generally cylindrical specimen blocks.

4. The system according to either claim 1 or 2, wherein each of said shaped cavities of said at least one specimen block storage module is shaped to receive generally flat specimen blocks.

5. The system according to either claim 1 or 2, wherein said underside of said at least one specimen block storage module is at least partially formed by a plurality of extensions each with a flat surface, each one of said flat surfaces being coplanar with each other of said flat surfaces, each of said extensions being formed in said closed end of each one of said plurality of shaped cavities.

6. The system according to claim 2, wherein said at least one specimen block storage module further comprises a laterally-extending rim, and said underside of said at least one specimen block storage module is at least partially formed by said laterally-extending rim.

7. The system according to either claim 1 or 2, wherein said means for securing said at least one specimen block storage module to a mounting surface is an adhesive coating on at least a portion of said underside of said at least one specimen block storage module.

8. The system according to either claim 1 or 2, wherein a double-sided adhesive sheet is affixed to at least a portion of said underside of said at least one specimen block storage module.

9. The system according to either claim 1 or 2, wherein each of said shaped cavities of said at least one specimen block storage module has associated locating indicia.

10. The system according to either claim 1 or 2, further comprising a removable cover for said at least one panel.

11. A specimen block storage module, comprising:
    (a) a plurality of indentations forming cavities shaped for receiving and retaining a plurality of specimen blocks regardless of the spatial orientation of the specimen block storage module;
    (b) an underside beneath said plurality of shaped cavities, and
    (c) means for securing the specimen block storage module to a mounting surface.

12. The specimen block storage module according to claim 11, wherein each of said shaped cavities comprises an open end and a closed end, and includes opposed structural projections formed at said open end of said cavity.

13. The specimen block storage module according to either claim 11 or 12, wherein each of said shaped cavities is shaped to receive generally cylindrical specimen blocks.

14. The specimen block storage module according to either claim 11 or 12, wherein each of said shaped cavities is shaped to receive generally flat specimen block sections.

15. The specimen block storage module according to either claim 11 or 12, wherein said means for securing said specimen block storage module to a mounting surface is an adhesive coating on at least a portion of said underside of said specimen block storage module.

16. The specimen block storage module according to either claim 11 or 12, wherein said underside is at least partially formed by a plurality of extensions each with a flat surface, each one of said flat surfaces being coplanar with each other of said flat surfaces, each of said extensions being formed in said closed end of each one of said plurality of shaped cavities.

17. The specimen block storage module according to either claim 11 or 12, further comprising a laterally-extending rim, and said underside of said specimen block storage module is at least partially formed by said laterally-extending rim.

18. The specimen block storage module according to either claim 11 or 12, wherein a double-sided adhesive sheet is affixed to at least a portion of said underside.

19. The specimen block storage module according to either claim 11 or 12, wherein each of said shaped cavities has associated locating indicia.

20. The combination of (1) a panel for mounting at least one specimen block storage module, said panel comprising a mounting surface for said at least one storage module, and means for securing said panel in a binder; (2) a removable cover for said panel; (3) and cooperative means on said panel and said cover for detachably securing said panel and said cover to one another.

21. The combination according to claim 20, wherein a ridge is formed around the area of said mounting surface in which said at least one specimen block storage module is to be mounted, and two pairs of opposed slots are formed in the outward surface of said ridge.

22. The combination according to claim 21, wherein two pairs of opposed indents are formed in said cover to engage said two pairs of opposed slots formed in said ridge.

23. The combination according to claim 22, wherein said cover further comprises at least one tab for facilitating the detachment of said cover from said panel.

24. The combination according to claim 22, wherein said cover further comprises means for securing said cover in a binder.

* * * * *